United States Patent
Voerman

(10) Patent No.: US 6,239,106 B1
(45) Date of Patent: May 29, 2001

(54) FAMILY OF PROTEASE INHIBITORS, AND OTHER BIOLOGIC ACTIVE SUBSTANCES

(75) Inventor: Gerard Voerman, Brasschaat (BE)

(73) Assignee: Clodica, S.A., Luxembourg (LU)

( * ) Notice: Subject to any disclaimer, the term of this patent is extended or adjusted under 35 U.S.C. 154(b) by 0 days.

(21) Appl. No.: 08/836,686

(22) PCT Filed: Oct. 27, 1995

(86) PCT No.: PCT/EP95/04223

§ 371 Date: Mar. 27, 1998

§ 102(e) Date: Mar. 27, 1998

(87) PCT Pub. No.: WO96/13585

PCT Pub. Date: May 9, 1996

(30) Foreign Application Priority Data

Oct. 28, 1994 (EP) ................................. 94 117053
Mar. 14, 1995 (EP) ................................. 95 103637

(51) Int. Cl.[7] ............................. A61K 38/00; C12N 9/48; C12N 1/20; C07H 21/04
(52) U.S. Cl. ........................... 514/13; 435/212; 435/213; 435/214; 435/215; 435/216; 435/217; 435/218; 435/219; 435/69.1; 435/252.3; 435/320.1; 536/23.2; 530/324; 530/350
(58) Field of Search ...................... 514/13; 435/212–219, 435/69.1, 252.3, 320.1; 536/23.2; 530/324, 350

(56) References Cited

U.S. PATENT DOCUMENTS 5,858,970 * 1/1999 Zeelon et al. ............................. 514/8

OTHER PUBLICATIONS

Lehman et al. [Protein Expression and Purification, (1993 Jun.) 4 (3)247–55].*

* cited by examiner

*Primary Examiner*—Tekchand Saidha
(74) *Attorney, Agent, or Firm*—Welsh & Katz, Ltd.

(57) ABSTRACT

The invention relates to novel protease-inhibitors which are obtainable from leeches. It also relates to uses thereof, for instance as a medicament, thus pharmaceutical preparations are provided, as are derivatives, mutants, genes encoding, vectors comprising and cells provided with such genes and/or vectors. In particular the invention relates to a family of proteinaceous protease-inhibitors having a molecular weight of about 5.5 kD and the following primary sequences: DDNCGGKVCSKGQLCHDGHCECTPIRCLI FCPNGFAVDENGCELPCSCKHQ, DDDCGGQVCSKGQ LCVDGQCKCTPIRCRIYCPKGFEVDENGCELPCTCLQ and DGNCGGQVCSKGQLCVDGQCKCTPIRCRIYCPK GFEVDENGCELPCTCLQ. This invention also relates to HIV-inhibitors and other therapeutically interesting, low molecular weight, and low antigenic substances from leeches.

14 Claims, 10 Drawing Sheets

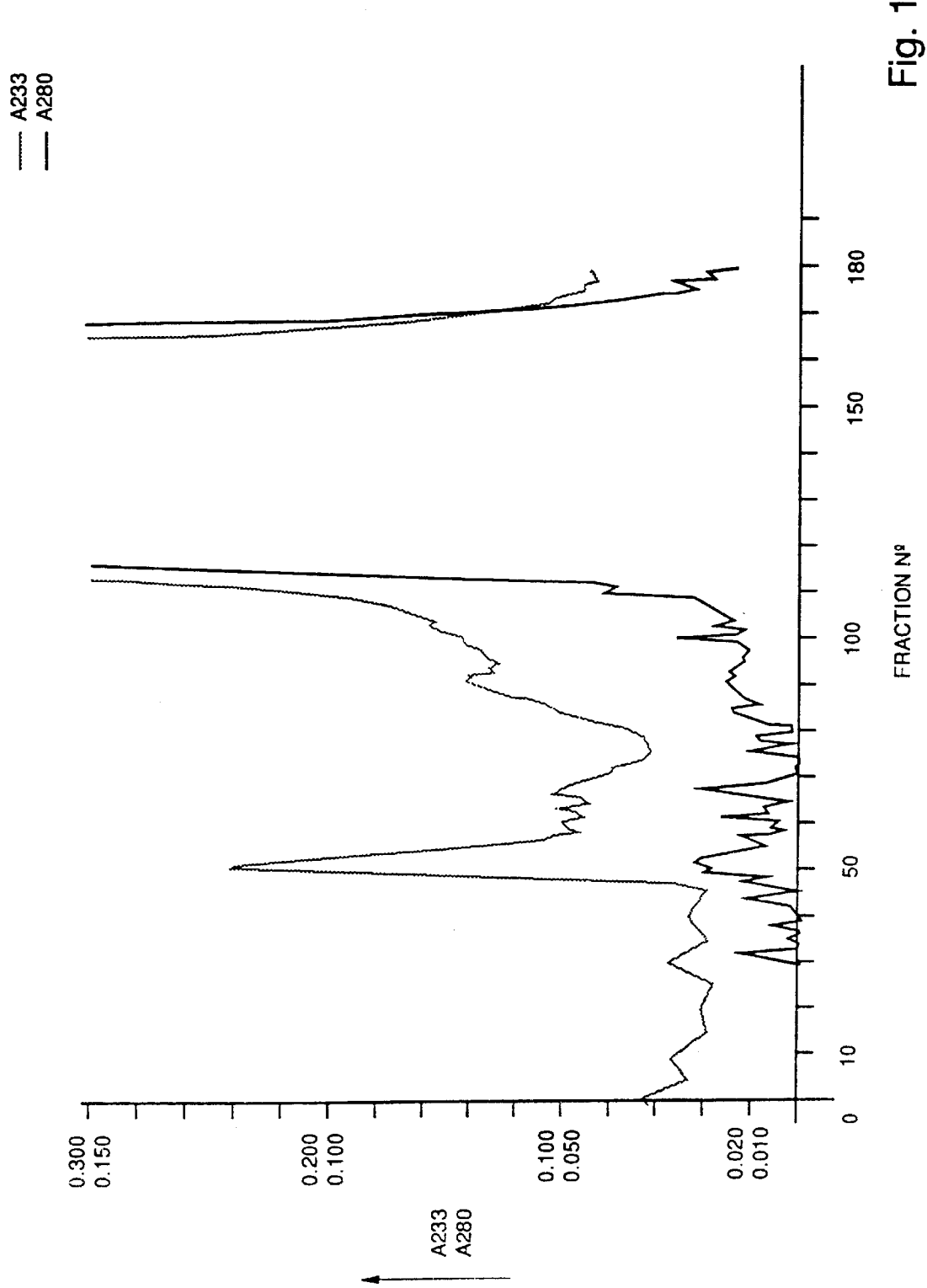

Fig. 2a

Figure 5:
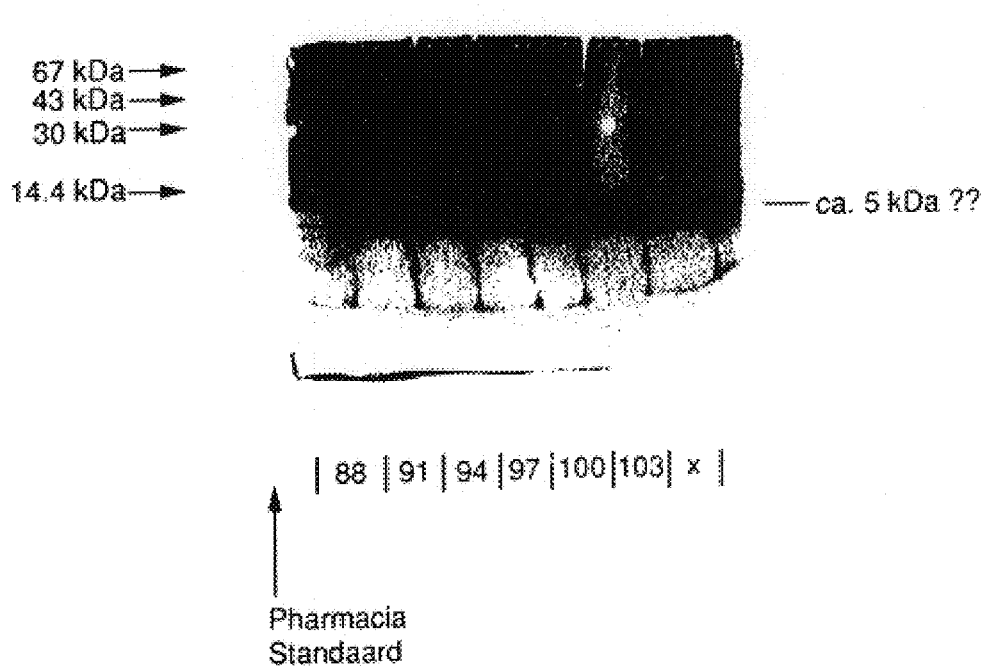

| No. | A280 | A233 | No. | A280 | A233 |
|-----|------|------|-----|------|------|
| 30 | 0,001 | .056 | 62 | .007 | .096 |
| 31 | 0,0 10 | .056 | 63 | .007 | .102 |
| 32 | 0.012 | .051 | 64 | .002 | .090 |
| 33 | -0,003 | .047 | 65 | .003 | .093 |
| 34 | -0,002 | .047 | 66 | .018 | .105 |
| 35 | 0.002 | .049 | 67 | .020 | .101 |
| 36 | -0,002 | .044 | 68 | .009 | .099 |
| 37 | -0,001 | .045 | 69 | .004 | .092 |
| 38 | 0.005 | .049 | 70 | .001 | .082 |
| 39 | -.002 | .046 | 71 | .001 | .081 |
| 40 | -.001 | .047 | 72 | .000 | .073 |
| 41 | -.001 | .043 | 73 | .000 | .068 |
| 42 | .002 | .042 | 74 | .000 | .063 |
| 43 | .013 | .042 | 75 | .010 | .063 |
| 44 | .006 | .043 | 76 | .002 | .064 |
| 45 | .000 | .040 | 77 | .008 | .065 |
| 46 | .003 | .042 | 78 | .009 | .066 |
| 47 | .013 | .054 | 79 | .002 | .072 |
| 48 | .007 | .114 | 80 | .002 | .075 |
| 49 | .020 | .208 | 81 | .007 | .087 |
| 50 | .019 | .242 | 82 | .010 | .094 |
| 51 | .022 | .240 | 83 | .014 | .102 |
| 52 | .021 | .217 | 84 | .014 | .106 |
| 53 | .018 | .182 | 85 | .009 | .108 |
| 54 | .013 | .152 | 86 | .012 | .116 |
| 55 | .007 | .126 | 87 | .013 | .125 |
| 56 | 009 | .109 | 88 | .014 | .130 |
| 57 | .013 | .104 | 89 | .015 | .136 |
| 58 | .003 | .096 | 90 | .016 | .142 |
| 59 | .006 | .099 | 91 | .014 | .140 |
| 60 | .005 | .100 | 92 | .015 | .135 |
| 61 | .017 | .093 | 93 | .013 | .131 |

A 280/233 absorption of Sephadex fractions 30-93

Fig. 2b

| No. | A280 | A233 | No. | A280 | A233 |
|---|---|---|---|---|---|
| 94 | .012 | .128 | 155 | 1,651 | >1 |
| 95 | .012 | .132 | 156 | 1,464 | 1,595 |
| 96 | .011 | .135 | 157 | 1,280 | 1,250 |
| 97 | .011 | .136 | 158 | 1,120 | 1,032 |
| 98 | .013 | .140 | 159 | 0,953 | .863 |
| 99 | .026 | .143 | 160 | 0,815 | .736 |
| 100 | .013 | .146 | 161 | .662 | .595 |
| 101 | .012 | .153 | 162 | .543 | .500 |
| 102 | .018 | .157 | 163 | .437 | .415 |
| 103 | .014 | .156 | 164 | .351 | .352 |
| 104 | .015 | .162 | 165 | .272 | .290 |
| 105 | .017 | .167 | 166 | .217 | .249 |
| 106 | .018 | .174 | 167 | .163 | .206 |
| 107 | .020 | .182 | 168 | .130 | .183 |
| 108 | .023 | .197 | 169 | .099 | .160 |
| 109 | .041 | .217 | 170 | .079 | .146 |
| 110 | .039 | .240 | 171 | .061 | .123 |
| 111 | .045 | .263 | 172 | .0 48 | .116 |
| 112 | .069 | .304 | 173 | .038 | .106 |
| 113 | .089 | .370 | 174 | .033 | .102 |
| 114 | .045 | .484 | 175 | .026 | .095 |
| 115 | .226 | .685 | 176 | .022 | .091 |
| 116 | .400 | 1,111 | 177 | .027 | .090 |
| 117 | .660 | >1 | 178 | .018 | .086 |
| 118 | .994 | >1 | 179 | .019 | .089 |
| 119 | 1.326 | >1 | 180 | .014 | .082 |
| 120 | 1.607 | >1 | 1 | | .066 |
| 121 | 1.902 | >1 | 5 | | .048 |
| 122 | >1 | >1 | 10 | | .054 |
| 123 | >1 | >1 | 15 | | .040 |
| 125 | >1 | >1 | 20 | | .042 |
| 130 | >1 | >1 | 25 | | .048 |

A 280/233 absorption of Sephadex fractions 94-180; and 1-25 fig. 3

| Fractie | A405 | Fractie | A405 |
|---|---|---|---|
| B+ | 0.450 | 156 | 0.172 |
| B- | 0.005 | 160 | 0.198 |
| 48 | 0.164 | 164 | 0.156 |
| 52 | 0.166 | 168 | 0.163 |
| 56 | 0.165 | 172 | 0.157 |
| 60 | 0.161 | 176 | 0.171 |
| 64 | 0.171 | 180 | 0.177 |
| 68 | 0.167 | | |
| 72 | 0.171 | | |
| 76 | 0.167 | | |
| 80 | 0.168 | | |
| 84 | 0.172 | | |
| 88 | 0.172 | | |
| 92 | 0.132 | | |
| 96 | 0.014 | | |
| 100 | 0.008 | | |
| 104 | 0.007 | | |
| 108 | 0.006 | | |
| 112 | 0.015 | | |
| 116 | 0.156 | | |
| 120 | 0.183 | | |
| 124 | 0.179 | | |
| 128 | 0.189 | | |
| 132 | 1.194 | | |
| 136 | 0.198 | | |
| 140 | 0.190 | | |
| 144 | 0.190 | | |
| 148 | 0.177 | | |
| 150 | 0.223 | | |

B+ = blank
0.1 M acetic acid,
with SAAAP
B- = blank
0.1 M acetic acid,
without SAAAP

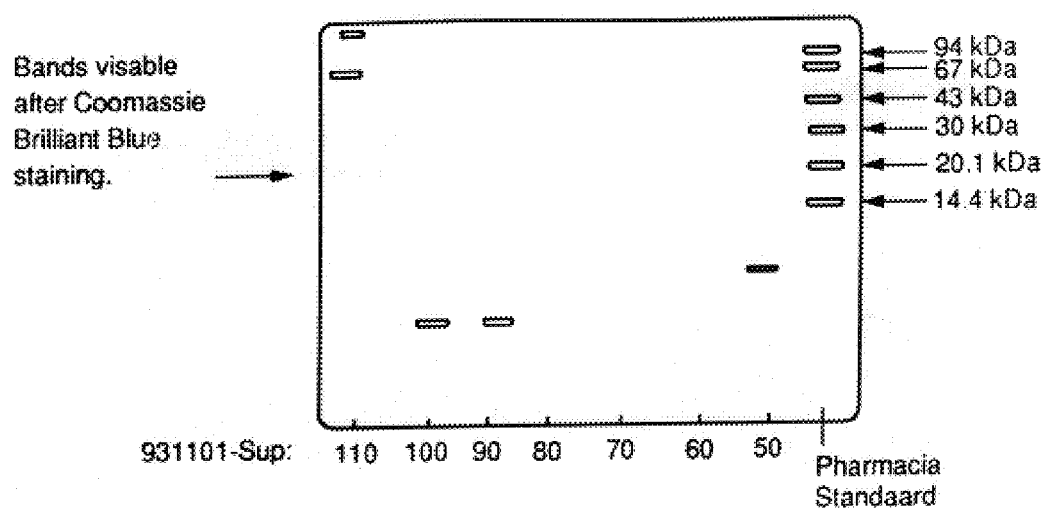
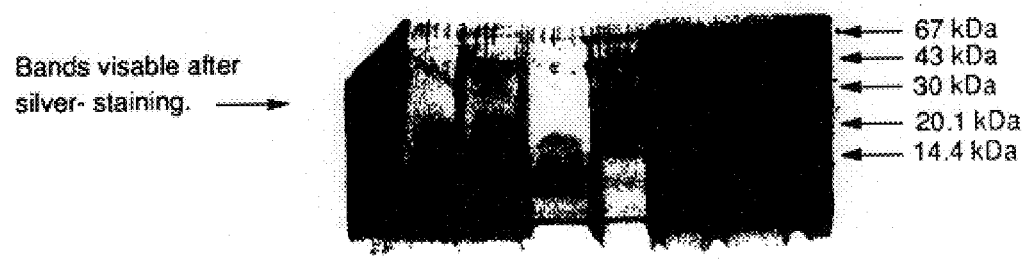
SPS-PAGE of Sepadex G-75 fractions of 931101-Sup
(GEL-1)
Fig. 4

SPS-PAGE of Sepadex G-75 fractions of
931101-Sup
(GEL-2)

SPS-PAGE of Sepadex G-75 fractions of
931101-Sup
(GEL-3)

Fig. 8a
Substance 1

| PRIMARY HIV-1 ISOLATE HIV$_{AMS}$ 37 | | | | | | |
|---|---|---|---|---|---|---|
| INOCULUM (TCID$_{50}$/ml): | $10^4$ | | | | | |
| Concentration of substance (µM) | CPE | | Day 7 | | Day 14 | |
| | Day 4 | Day 7 | p24 (µg/ml) | Percentage Inhibition | p24 (µg/ml) | Percentage Inhibition |
| 0 | ++ | +++ | 1.00 | | 0.56 | |
| 0.125 | +++ | +++ | 0.70 | 30 | 0.48 | 14 |
| 0.25 | +++ | +++ | 0.72 | 28 | 0.45 | 20 |
| 0.5 | ++ | +++ | 0.65 | 35 | 0.46 | 18 |
| 1.0 | ± | +++ | 0.60 | 40 | 0.38 | 32 |

Fig. 8b
Substance 1

| PRIMARY HIV-1 ISOLATE HIV$_{AMS}$ 55 | | | | | | |
|---|---|---|---|---|---|---|
| INOCULUM (TCID$_{50}$/ml): | $10^4$ | | | | | |
| Concentration of substance (µM) | CPE | | Day 7 | | Day 14 | |
| | Day 4 | Day 7 | p24 (µg/ml) | Percentage Inhibition | p24 (µg/ml) | Percentage Inhibition |
| 0 | +++ | +++ | 1.43 | | 0.63 | |
| 0.125 | +++ | +++ | 1.25 | 13 | 0.64 | -2 |
| 0.25 | ++ | +++ | 1.05 | 27 | 0.42 | 33 |
| 0.5 | ++ | +++ | 1.16 | 19 | 0.51 | 19 |
| 1.0 | +++ | +++ | 1.00 | 30 | 0.41 | 35 |

Fig. 8c
Substance 2

| PRIMARY HIV-1 ISOLATE HIV$_{AMS}$ 37 | | | | | | |
|---|---|---|---|---|---|---|
| INOCULUM (TCID$_{50}$/ml): | $10^4$ | | | | | |
| Concentration of substance (μM) | CPE | | Day 7 | | Day 14 | |
| | Day 4 | Day 7 | p24 (μg/ml) | Percentage Inhibition | p24 (μg/ml) | Percentage Inhibition |
| 0 | ++ | +++ | 0.66 | | 0.41 | |
| 0.125 | + | +++ | 0.67 | 0 | 0.39 | 5 |
| 0.25 | + | +++ | 0.61 | 8 | 0.31 | 24 |
| 0.5 | ++ | +++ | 0.55 | 17 | 0.26 | 37 |
| 1.0 | ++ | +++ | 0.55 | 17 | 0.24 | 41 |

Fig. 8d
Substance 2

| PRIMARY HIV-1 ISOLATE HIV$_{AMS}$ 55 | | | | | | |
|---|---|---|---|---|---|---|
| INOCULUM (TCID$_{50}$/ml): | $10^4$ | | | | | |
| Concentration of substance (μM) | CPE | | Day 7 | | Day 14 | |
| | Day 4 | Day 7 | p24 (μg/ml) | Percentage Inhibition | p24 (μg/ml) | Percentage Inhibition |
| 0 | ++ | +++ | 1.25 | | 0.45 | |
| 0.125 | +++ | +++ | 1.25 | 0 | 0.45 | 0 |
| 0.25 | +++ | +++ | 1.19 | 5 | 0.36 | 20 |
| 0.5 | +++ | +++ | 1.23 | 2 | 0.42 | 7 |
| 1.0 | ++ | +++ | 1.14 | 9 | 0.37 | 18 |

SEQUENCE LISTING

<160> NUMBER OF SEQ ID NOS: 11

<210> SEQ ID NO: 1
<211> LENGTH: 171
<212> TYPE: DNA
<213> ORGANISM: Limnatis nilotica
<220> FEATURE:
<221> NAME/KEY: misc_feature
<222> LOCATION: (1)..(180)
<223> OTHER INFORMATION: nucleic acid molecule and some alternatives
      thereof, whereby R=A/G, N=A/C/G/T, Y=C/T, D=A/G/T.

<400> SEQUENCE: 1
ctrctrttra crccnccntt ycanacragn tcrttyccng tyaayganac rgtrctrccn     60
gtracrctya crtgnggnta dgcntcyacr aaygantada aracrcgntt rccnaarcgn    120
canctrctyt trccnacrct yaayganggn acragntcra crttygtrgt y             171

<210> SEQ ID NO: 2
<211> LENGTH: 51
<212> TYPE: PRT
<213> ORGANISM: Limnatis nilotica
<220> FEATURE:
<221> NAME/KEY: PEPTIDE
<222> LOCATION: (1)..(30)
<223> OTHER INFORMATION: part of a  proteinaceous or polypeptide-like
      substance from Limnatis nilotica

<400> SEQUENCE: 2

Asp Asp Asn Cys Gly Gly Lys Val Cys Ser Lys Gly Gln Leu Cys His
 1               5                  10                  15

Asp Gly His Cys Glu Cys Thr Pro Ile Arg Cys Leu Ile Phe Cys Pro
             20                  25                  30

Asn Gly Phe Ala Val Asp Glu Asn Gly Cys Glu Leu Pro Cys Ser Cys
         35                  40                  45

Lys His Gln
     50

<210> SEQ ID NO: 3
<211> LENGTH: 50
<212> TYPE: PRT
<213> ORGANISM: Limnatis nilotica
<220> FEATURE:
<221> NAME/KEY: PEPTIDE
<222> LOCATION: (1)..(50)
<223> OTHER INFORMATION: part of a proteinaceous or polypeptide-like
      substance from Limnatis nilotica

<400> SEQUENCE: 3

Asp Asp Asp Cys Gly Gly Gln Val Cys Ser Lys Gly Gln Leu Cys Val
 1               5                  10                  15

Asp Gly Gln Cys Lys Cys Thr Pro Ile Arg Cys Arg Ile Tyr Cys Pro
             20                  25                  30

Lys Gly Phe Glu Val Asp Glu Asn Gly Cys Glu Leu Pro Cys Thr Cys
         35                  40                  45

Leu Gln
     50

<210> SEQ ID NO: 4
<211> LENGTH: 50
<212> TYPE: PRT
<213> ORGANISM: Limnatis nilotica
<220> FEATURE:

```
<221> NAME/KEY: PEPTIDE
<222> LOCATION: (1)..(50)
<223> OTHER INFORMATION: part of a proteinaceous or peptide-like
      substance from Limnatis nilotica

<400> SEQUENCE: 4

Asp Gly Asn Cys Gly Gly Gln Val Cys Ser Lys Gly Gln Leu Cys Val
 1               5                  10                  15

Asp Gly Gln Cys Lys Cys Thr Pro Ile Arg Cys Arg Ile Tyr Cys Pro
                20                  25                  30

Lys Gly Phe Glu Val Asp Glu Asn Gly Cys Glu Leu Pro Cys Thr Cys
            35                  40                  45

Leu Gln
    50

<210> SEQ ID NO: 5
<211> LENGTH: 50
<212> TYPE: PRT
<213> ORGANISM: Limnatis nilotica
<220> FEATURE:
<221> NAME/KEY: PEPTIDE
<222> LOCATION: (1)..(50)
<223> OTHER INFORMATION: part of a proteinaceous of peptide-like
      substance from Limnatis nilotica

<400> SEQUENCE: 5

Asp Asp Asp Cys Gly Gly Gln Val Cys Ser Lys Gly Gln Leu Cys Val
 1               5                  10                  15

Asp Gly Gln Cys Lys Cys Thr Pro Ile Arg Cys Arg Ile Tyr Cys Pro
                20                  25                  30

Lys Gly Phe Glu Val Asp Glu Asn Gly Cys Glu Leu Pro Cys Thr Cys
            35                  40                  45

Lys Gln
    50

<210> SEQ ID NO: 6
<211> LENGTH: 50
<212> TYPE: PRT
<213> ORGANISM: Limnatis nilotica
<220> FEATURE:
<221> NAME/KEY: PEPTIDE
<222> LOCATION: (1)..(50)
<223> OTHER INFORMATION: part of a proteinaceous or peptide-like
      substance from Limnatis nilotica

<400> SEQUENCE: 6

Asp Gly Asn Cys Gly Gly Gln Val Cys Ser Lys Gly Gln Leu Cys Val
 1               5                  10                  15

Asp Gly Gln Cys Lys Cys Thr Pro Ile Arg Cys Arg Ile Tyr Cys Pro
                20                  25                  30

Lys Gly Phe Glu Val Asp Glu Asn Gly Cys Glu Leu Pro Cys Thr Cys
            35                  40                  45

Lys Gln
    50

<210> SEQ ID NO: 7
<211> LENGTH: 37
<212> TYPE: PRT
<213> ORGANISM: Limnatis nilotica
<220> FEATURE:
<221> NAME/KEY: PEPTIDE
<222> LOCATION: (1)..(37)
<223> OTHER INFORMATION: sequence of one other single molecule isoform,
      found in peak 7 ( figure 7)
```

<400> SEQUENCE: 7

Asp Asp Asp Cys Gly Gly Gln Val Cys Ser Lys Gly Gln Leu Cys His
 1               5                  10                  15

Asp Gly His Cys Glu Cys Thr Pro Ile Arg Cys Leu Ile Tyr Cys Pro
            20                  25                  30

Asn Phe Val Asp Glu
        35

<210> SEQ ID NO: 8
<211> LENGTH: 41
<212> TYPE: PRT
<213> ORGANISM: Limnatis nilotica
<220> FEATURE:
<221> NAME/KEY: PEPTIDE
<222> LOCATION: (1)..(41)
<223> OTHER INFORMATION: sequence of another isoform, which was found
      to be a mixture of two molecules, in peak 9 (figure 7)

<400> SEQUENCE: 8

Asp Asp Asp Cys Gly Gly Lys Val Cys Ser Lys Gly Gln Leu Cys Val
 1               5                  10                  15

Asp Gly His Cys Glu Cys Thr Pro Ile Arg Cys Leu Ile Tyr Cys Pro
            20                  25                  30

Asn Gly Phe Ala Val Glu Asn Gly Cys
        35                  40

<210> SEQ ID NO: 9
<211> LENGTH: 41
<212> TYPE: PRT
<213> ORGANISM: Limnatis nilotica
<220> FEATURE:
<221> NAME/KEY: PEPTIDE
<222> LOCATION: (1)..(41)
<223> OTHER INFORMATION: sequence of another isoform, which was found to
      be a mixture of two molecules, in peak 9 (figure 7)

<400> SEQUENCE: 9

Asp Gly Asn Cys Gly Gly Gln Val Cys Ser Lys Gly Gln Leu Cys Val
 1               5                  10                  15

Asp Gly Gln Cys Lys Cys Thr Pro Ile Arg Cys Leu Ile Tyr Cys Pro
            20                  25                  30

Asn Gly Phe Ala Val Glu Asn Gly Cys
        35                  40

<210> SEQ ID NO: 10
<211> LENGTH: 16
<212> TYPE: PRT
<213> ORGANISM: Artificial Sequence
<220> FEATURE:
<223> OTHER INFORMATION: Description of Artificial Sequence: synthetic
      linear peptide mimick of residues 23 to 38 of L.
      nilotica elastase inhibitor
<221> NAME/KEY: MOD_RES
<222> LOCATION: (5)
<223> OTHER INFORMATION: Abu
<221> NAME/KEY: MOD_RES
<222> LOCATION: (9)
<223> OTHER INFORMATION: Abu

<400> SEQUENCE: 10

Thr Pro Ile Arg Xaa Leu Ile Phe Xaa Pro Asn Gly Phe Ala Val Asp
 1               5                  10                  15

-continued

```
<210> SEQ ID NO: 11
<211> LENGTH: 16
<212> TYPE: PRT
<213> ORGANISM: Artificial Sequence
<220> FEATURE:
<221> NAME/KEY: MOD_RES
<222> LOCATION: (5)
<223> OTHER INFORMATION: Abu
<221> NAME/KEY: MOD_RES
<222> LOCATION: (9)
<223> OTHER INFORMATION: Abu
<223> OTHER INFORMATION: Description of Artificial Sequence: Synthetic
      linear peptide mimicking residues 23 to 38 of L.
      nilotica trypsin inhibitor

<400> SEQUENCE: 11

Thr Pro Ile Arg Xaa Arg Ile Tyr Xaa Pro Lys Gly Phe Glu Val Asp
 1               5                  10                  15
```

FAMILY OF PROTEASE INHIBITORS, AND OTHER BIOLOGIC ACTIVE SUBSTANCES

CROSS-REFERENCE TO RELATED APPLICATIONS

This application is the U.S. National Stage of International Application No. PCT/EP95/04223, filed Oct. 27, 1995 under 35 U.S.C. 0371.

The present invention relates to certain novel compounds which have protease inhibitory activity, as well as compounds derived therefrom and compositions comprising such compounds, and other biologically active substances. More specifically the invention relates to such compounds which are polypeptide-like or of a proteinaceous nature and of polysaccharide derivates and/or glyco-poly saccharide. The invention especially relates to such compounds and compositions and uses thereof obtainable from leeches.

The invention further relates to therapeutic uses of the novel protease inhibitors. An illustrative example of such a use is given below.

Several diseases, like emphysema, arthritis, gingivitis, periodontitis and other inflammatory conditions are associated with tissue destruction caused by the enzyme human neutrophil elastase (HNE). HNE is a serine protease which is capable of solubilising fibrous proteins like elastin and collagen. HNE is mainly present in the azurophilic granules of neutrophil leucocytes. Under normal physiological conditions, the proteolytic activity of the enzyme is kept under control by an excess of inhibitors present in plasma and other secretions. However, some disorders result in a local deficiency or inactivation of inhibitor which leads to an imbalance in the ratio of inhibitor to elastase, resulting in tissue destruction.

The balance may be restored employing protease inhibitors, for instance those provided by the invention.

Furthermore, in the replication cycle of HIV, the proteolytic cleavage of the gag and env precursors is an important step. Development of inhibitors of these proteases is a rationale in anti-viral drug development. Study-objectives evaluating anti-viral capacity of potential substances is therefore valuable.

Various substances extracted from leeches are known to have useful biological activity. These were reviewed by Sawyer, (Sawyer, 1990). Essentially two groups of activity can be recognised. The first group comprises antithrombotic and fibrinolytic activities, the second group comprises enzymes and inhibitors. Well known representatives of the first group include for instance Hirudin, a thrombin inhibitor, (Markwardt, 1956; 1988; Petersen, et al, 1984); Hementin, a fibrinolytic agent (Budzynski, et al, 1981; Kirschbaum & Budzynski, 1990); Antistasin, an inhibitor of coagulation factor Xa (Gasic, et al, 1983), which was reported to have antimetastatic properties as well; Gilanten, another factor X inhibitor (Condra, et al, 1989; Blankenship, et al, 1990). Representatives of the second group are: Bdellin, an inhibitor of trypsin and plasmin (Fritz & Krejci, 1976); Eglin, an inhibitor of chymotrypsin, elastase and Cathepsin G (Seemuller, 1979); Orgelase, an hyaluronidase (Sawyer, 1986).

More recently several additions in this field have been published in patent literature: A fibrinolytic enzyme isolated from Hirudo medicinalis, which splits Glutamyl-Lysin sequences (EP 0502876); a platelet adhesion inhibitor, isolated from Hirudo medicinalis, which inhibits collagen-induced platelet aggregation (EP 0552269); a thrombin inhibitor from the leech Hirudinaria manillensis (PCT/GB89/01345); an inhibitor of platelet aggregation from leeches from the Hirudinidae family (EP 0348208); an anticoagulant/modulator factor isolated from Hirudo medicinalis (EP 0352903); A chymotrypsin- and elastase inhibitor from Hirudinaria manillensis (PCT/NL90/00046).

This invention provides novel protease-inhibitors and other biologically active substances, as well as pharmaceutical and cosmetic preparations containing one or more of these compounds. In one aspect the invention provides substances having protease inhibiting activity obtainable from Limnatis Nilotica or fragments or derivatives of such substance having similar activity.

Such substances can be derived from all body parts and secretions of the leech, inclusive saliva and gut-, intestinal- and skin secretions and mucus. These novel Elastase/chymotrypsin- and trypsin-inhibitors according to part of this invention can be typically isolated from leech tissue by solvent extraction-techniques; alternatively they may be isolated from leech secretions (such as leech saliva), although the invention is not limited to specific ways of obtaining the novel protease-inhibitors. In a further embodiment the invention provides such a novel protease inhibitor which is of a proteinaceous or polypeptide-like nature. Preferably said proteinaceous substance includes at least a part of the following amino acid sequence: (1; SEQ ID NO:2)

```
                              5                10
(N-terminal) Asp-Asp-Asn-Cys-Gly-Gly-Lys-Val-Cys-Ser-Lys-Gly-    (1; SEQ ID NO:2)
Gln- 15                20                25
Leu-Cys-His-Asp-Gly-His-Cys-Glu-Cys-Thr-Pro-Ile-Arg-Cys-Leu- 45                50
Leu-Pro-Cys-Ser-Cys-Lys-His-Gln: (Carboxy-terminal) or           (2; SEQ ID NO:)

1            5                  10                 15
Asp-Asp-Asp-Cys-Gly-Gly-Gln-Val-Cys-Ser-Lys-Gly-Gln-Leu-Cys-
     Gly Asn 16              20                25                 30
Val-Asp-Gly-Gln-Cys-Lys-Cys-Thr-Pro-Ile-Arg-Cys-Arg-Ile-Tyr- 31              35                40                 45
Cys-Pro-Lys-Gly-Phe-Glu-Val-Asp?-Glu-Asn-Gly-Cys-Glu-Leu-Pro- 46              50
Cys-Thr-Cys-Lys?-Gln?
``` although it will be clear that the activities are the really important features of this invention, so that mutations, isoforms, derivatives, such as salts, fragments or even peptidomimetics and anti-idiotypic or catalytic antibodies are also a part of this invention.

For the definition of isoforms or mutants, one has to understand that by biologic evolution enzymatic and other systems active molecules are subject to continuous phylogenetic development. It is in this understanding, that we define isoforms or mutant forms of these molecules. The primary structure (1) as reported here is one of three or four isoforms, which have large conformity, and are being defined by molecule weight and amino acid sequence. The same may be true for (2).

A number of isoforms of (1) are identified below. The novel protease-inhibitors can be applied in the known applications for such substances. They can be suitably formulated into pharmaceutical compositions, which may comprise suitable excipients for administration. Administration may be accomplished in any suitable manner, although for proteinaceous substances in systemic applications parenteral routes are preferred. Dosages for these substances can be taken from the literature and designed on the basis of specific activities of the substances, the molecular weight of these substances, the weight of the subject to be treated, the kind of application, etc. Dosages will usually lie between 0.1 µg/kg and 10 mg/kg bodyweight.

Nucleic acid molecules encoding substances according to this invention are also provided. They can be used for detection of the gene encoding the substance, for expression of the substance in suitable host cells and for preparing site-directed mutants. Site-directed mutations are often useful in that they can increase activity and/or stability of the encoded substance.

There are many suitable expression systems for expression of substances according to the invention. Although expression in host cells is preferred, it is also possible to employ cell-free expression systems. Suitable host cells may be prokaryotic or eukaryotic since it appears that the proteinaceous substances according to the invention are not glycosylated or modified post-translationally in any other way, although a signal sequence may be present. Usually a nucleic acid to be expressed is provided in a vehicle for expression, such as a vector, whereby regulatory elements are provided, such as promoters, enhancers, and the like.

A nucleic acid molecule and some alternatives thereof which encode a substance according to the invention are given in SEQ ID NO:1 below: CTR CTR TTR ACR CCN CCN TTY CAN ACR AGN TCR TTY CCN GTY AAY GAN ACR GTR CTR CCN GTR ACR CTY ACR TGN GGN TAD GCN TCY ACR AAY GAN TAD AAR ACR CGN TTR CCN AAR CGN CAN CTR CTY TTR CCN ACR CTY AAY GAN GGN ACR AGN TCR ACR TTY GTR GTY whereby R=A/G, N=A/C/G/T, Y=C/T, D=A/G/T, or a sequence having 70% homology therewith.

BRIEF DESCRIPTION OF THE DRAWINGS

FIG. 1 shows the absorbance response, monitored at 233 and 280 nanometers, of the column effluent by fraction number from a Sephadex G-75 column chromatography of the 0.1 M acetic acid solution of resuspended lyophilized ethanol extract of dehydrated *Limnatis nilotica*.

FIGS. 2*a* and 2*b* are the same data as FIG. 1 in table form for Sephadex G-75 column fractions 30–93 (FIG. 2*a*), and fractions 94–180 and 1–25 (FIG. 2*b*).

FIG. 3 is a table showing the absorbance response, monitored at 405 nanometers, from the elastase inhibition assay on the chromatographic fractions from the Sephadex G-75 separation and two enzyme-free control reactions, B+is the blank of 0.1 M acetic acid with the elastase substrate SAAAP and B- is the blank of 0.1 M acetic acid without the elastase substrate SAAAP. Inhibition was found at fraction numbers 92 to 116.

FIGS. 4–6 show SDS-Page gel electrophoretic data used in estimating the molecular mass of polypeptides in fractions from the Sephadex G-75 column. Fractions 50, 60, 70, 80, 90, 100 and 110 of the Sephadex G-75 gel filtration were used for Gel 1 (FIG. 4), fractions 88, 91, 94, 97, 100 and 103 were used for Gel 2 (FIG. 5), and fractions 106, 109, 112, 115, 118 and 121 were used for Gel 3 (FIG. 6). It was found that in the area of elastase inhibition (from fractions 92 to 116) molecular masses were estimated at ca. 5 kDa (see fraction 106 and 109 in Gel 3 (FIG. 6).

FIG. 7 shows a HPLC chromatograph of fraction 15 from an immobilized anhydrochymotrypsin separation of the pooled Sephadex G-75 fractions 95 to 133. Fraction 15 was the only fraction that exhibited elastase inhibition activity.

FIGS. 8*a* to 8*d* show tables of data from studies of the activity of Fabsin against HIV-1 and HIV-2 isolates in peripheral blood mononuclear cells (PBMC) and primary macrophages as describe hereinafter. Both substance I (Fahsin E 1-4 and Fahsin T1-2; FIGS. 8*a* and 8*b*) and substance 2 (total leech body extract; FIGS. 8*c* and 8*d*) exhibited a cytopathic effect (CPE) based on synctia formation and the percentage inhibition of p24 antigen production from various inoculation amounts were calculated.

Experimental

During applicants' routine research work with cultures of various bacteria-species, screening methods for new antibiotics were used. While researching on the bacterium Aeromonas hydrophila species, which is a common bacteria from freshwater fish, waterfowl and leeches, an "auto"-antibiotic effect on Aeromonas isolated from leeches was surprisingly found. Blood nutrient plates ented with monocultures of *A. hydrophila* showed blank and developing areas, where enting was performed. It appeared that the blank areas were contaminated with some substances from the host (leeches), which prohibited bacterial growth in the contaminated areas. After further searching this activity seemed to arise from body-derived substances of the leech under investigation, which was harbouring the colony of Aeromonas. Applicant subsequently identified the original secretive elements of the leech body, isolated and purified the said factors, and discovered other biologic activities from this family of substances, which was named Fahsin. It was soon clear, that besides the said antibiotic effect, the substance was also biologically active as a protease inhibitor. The species of leech in which the substance was found belongs to the family of hirudinidae, and was designated as *Limnatis nilotica*. The said purification of the substance finally revealed a new family of proteins, which was not earlier described. This family of proteins comprises 50/51 amino acids, and they occur in various isoforms, where substitutions have taken place in the structure at various places as described.

Other substances having a low antigenic or non-antigenic effect when used as therapeuticum were isolated.

L Nilotica (Savigny, 1820, as following from Autrum 1936) is described as a "nasal leech" or horse leech (Mouquin-Tandon 1846). It was signalled to be present in the whole littoral area of the Mediteranean (Harant, 1929; Jarry, 1959). It lives in spring fountains and "oueds", and feeds on cattle, dogs and man ( Blaise, 1874/5; Neveu & Lemaire, 1938; Turner, 1969; Keegan, et al, 1970).

Amazingly, the feeding habits of this leech differ from other haemotophaguous leeches. It remains attached to its host (nasal—and laryngeal cavity) for prolonged periods (weeks subs. months). The animal feeds whenever it feels like doing so on its host repeatedly. We have observed that drinking cattle was infected with these leeches, which did not drop off while the cattle was drinking water. Only thick, fat, adult-size leeches do drop off at such occasions. Therefore, it is clear that this species of leech is mostly free of antigenic or immunogenic substances in its mucus or salivary gland product. Reports of host animals dying from this species of leech mention anaemia as a common cause, but to our knowledge no direct antigenic effect has been described.

The cycle of development of these leeches from hatchling to the reproductive phase spans over a few months in summertime only (Ghedia, 1984).

It was further observed, that these leeches, held in captivity, could be fed by heparinized blood from the slaughterhouse in animal gut preparations. Sacrificed leeches which did not feed on blood for several months, still contained more or less liquid blood in crop and gut. Therefore, these leeches must produce anticoagulant substances.

We further observed that this species of leech, held in captivity, was able to feed on blood clots. Several leeches did grow from hatchling to full-size leech under this regimen. After feeding, the remains of the blood clots are literally pierced. Therefore, we believe, that these leeches also produce substances to dissolve blood clots, f.e. by dissolving fibrin.

The present description reveals the unique primary sequence of the protein of formula (1), subject of this invention, its isolation and purification, its specific activities, its production through gene cloning and expression. Applicant specifically intends that this protein Fahsin, as invented, and described herein, includes such substance however produced, be it through sequential and on block synthesis or through gene cloning and expression.

The present invention also provides the primary sequence of the proteins/peptides of formula (2) and its specific activities (especially the inhibition of trypsin and plasmin). These peptides belonging to the Fahsin family of course also belong to the invention, regardless of their origin or way of production.

Description of isolation

1. Frozen *Limnatis nilotica* (300 g) were dehydrated in 94% ethylalcohol at room temperature: using three changes of total 400 ml. 100 ml of the ethanol extract was lyophilized in vials, after adding 300 ml destillated water. (One can also, as an alternative, use the chopped heads of these leeches, or use activated mucus secretions from the live leeches, by immersing them for one hour in 150 mM NaCl, 10 mM Arginin and 20 mM Phosphate buffer, at pH 7.0 at room temperature, or immersing the live leeches in 4% ethylalcohol for ten minutes, and collecting the large mucus secretions then produced) and thereafter lyophilized). All methods resulting in obtaining lyophilized base material.

2. Prior lyophilized base material underwent solubility tests after resuspension of the base material in 1) 0.1M Acetic Acid, 2) 50% Acetic Acid and 3) 0.1M Ammoniumbicarbonate and after centrifugation of the various suspensions, supernatants and pellets (after resuspension). Thereafter these were tested on the presence of protein by analytical sequence analysis (Edman degradation with automated sequenator Applied Biosystems, Model 477A) (Edman, 1956; Ilse & Edman, 1963), by applying protocolls, reagentia, chemicals and materials from Applied Biosystems (Warrington, UK and Foster City, Calif., USA) (Hewick, et al, 1981).It was investigated if biologic activity included anti-elastase as the described "auto-antibiotic effect" of A. hydrophila. Therefore, tests on inhibition of elastase activity were executed with dried samples of 20 µl of supernatant and resuspension of pellet of the base material on elastase (Boehringer) and SAAAP (Fluka) as chromogenic substrate, and 0.1 M Tris/HCl pH 8.2 as assay buffer. Based on the results obtained with the different solutions, and the inhibition of elastase, it was decided to use 0.1 M Hac as solution for the lyophilized base material and thereafter as eluens for gel filtration.

3. 15% of the base material was resuspended in 0.1M Hac, centrifuged twice and reassembled (volume ca. 28 ml). This was thereafter passed on a Sephadex G-75 column (length 180 cm, diameter 1.85 cm, eluens 0.1M Hac, fraction size ca 5 ml, flow adjusted at ca. 0.75 ml/min. A total of 180 fractions were sampled and absorbtion measured at 233 nm and 280 nm (for results see FIGS. 1 and 2).

Tests on inhibition of elastase activity were measured every 4 fractions on fractions no's 48 to 180, in accordance with the measurements under 2 hereabove. Inhibition was found at fractions no's 92 to 116. (FIG. 3).

An analytical test sequence analysis was run on 200 µl from fraction no. 105 in order to estimate the quantity of protein available. Signals present indicated a level of ca. 50 pmol, which indicates proteins/peptides at a level of 2.5 nmol, accepting 50% from initial yield.

Figure 6:
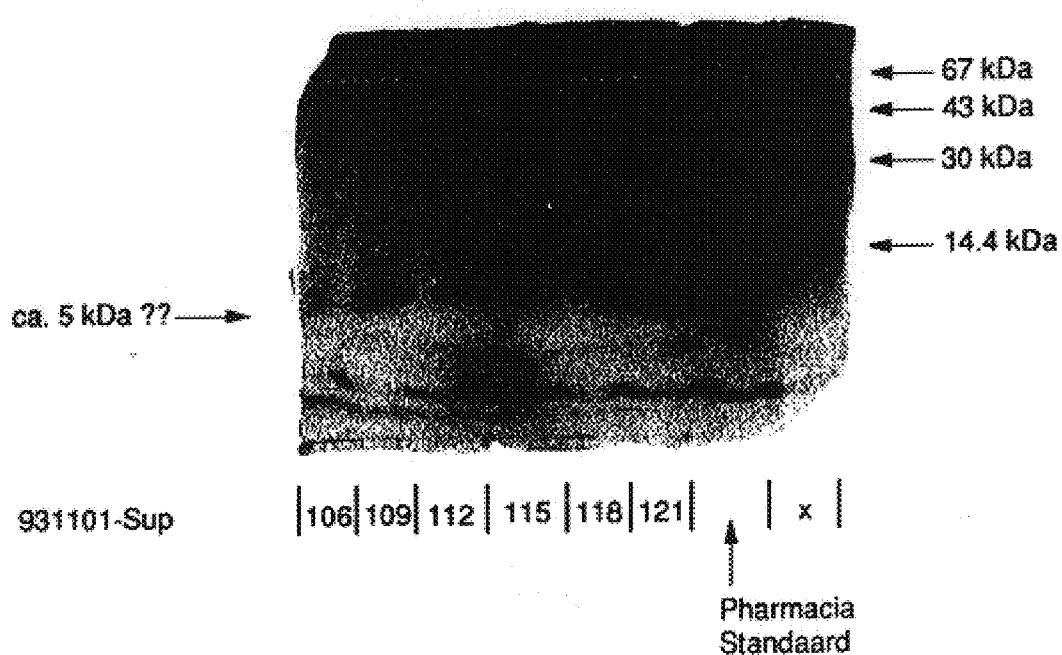

A further estimate of molecular mass was performed on fractions from the Sephadex column with SDS-Page. Results are presented on gels no 1, 2 and 3 (FIGS. 4, 5 and 6). Fractions 50, 60, 70, 80, 90, 100 and 110 of the Sephadex G-75 gelfiltration were used for Gel 1 (FIG. 4), fractions 88, 91, 94, 97, 100 and 103 were used for Gel 2 (FIG. 5) and fractions 106, 109, 112, 115, 118 and 121 were used for Gel 3 (FIG. 6). It was found that in the area of elastase inhibition (from fractions 92 to 116) molecular masses were estimated at ca. 5 kDa (see fraction 106 and 109 in Gel 3).

A pool was thereafter made from fractions containing no's 95 to 113 for further studies with:

4. Anhydrochymotrypsin column chromatography was performed on the previously pooled fraction no's 95 to 113. This pool was suspended in 6 ml 0.05 M Tris/HCl buffer, pH 8.2, containing 0.02 Ca $Cl_2$ and 0.02 % Na-azide, thereafter centrifuged. The remaining pellet was resuspended with 50 µl 8M ureum plus 950 µl $H_2O$. 10 µl of the resuspended pellet and 10 µl supernatant were passed for analytical sequence-analysis. After comparison of the results, it was concluded, that 5–10% of the protein as found in supernatant was present in the pellet. Inhibition of elastase could only be demonstrated with supernatant. Therefore, further proceedings took place with supernatant only.

A portion of 50% of the pooled fractions 95 to 113 (ca. 3 ml) was chromatographed over 1.5 ml "immobilized Anhydrochymotrypsin" (Pierce, Rockford Ill., USA, nr 20185) over a polystyrene-column (Pierce, Rockford Ill. USA), following the instructions from the manufacturer (binding buffer: 0.05M Tris-HCl buffer, pH 8.2, with 0.02M $CaCl_2$, 0.02% Na-azide; first elution buffer: 0.1 formic acid, pH 2.5; second elution buffer: 0.05M Tris-HCl, pH 8.2, with 0.02M $CaCl_2$, 0.02 Na-azide and 5M NaSCN; flow ca. 9.2 ml/hr; temp. 4° C., fraction size: ca 2 ml).The portion was eluted, after loading, with 30 ml binding buffer (fractions 1–17), 30 ml first elution buffer (fractions 18–31) 15 ml second elution-buffer ( fractions 32–40) and 6 ml binding buffer (fractions 41–43). These fractions were then tested on elastase inhibition activity by the standard elastase assay (as follows)

Elastse inhibition assay

The principle of the assay resides in inhibition of elastase (Boehringer, 1027891) activity on the chromogenic substrate SAAAP (Fluka, nr. 85975) as measured at 405 nm spectophotometrically by monitoring release of the p-nitroaniline group during substrate digestion.

Preparation of Solution:

Assay buffer: 0.1M Tris/HCl pH 8.2, 1M NaCl.

Elastase: 40 µg/ml in $H_2O$.

Substrate: 1.0 mM SAAAP in $H_2O$.

Glacial Acetic Acid 50%: diluted in $H_2O$.

Assay procedure:

Reaction in tubes (Eppendorf), containing 100 µl assay buffer, 50 µl sample elastase inhibitor, 50 µl elastase solution was started by addition of SAAAP (25 µl, 1 mM) and incubated at 25° C. for 30 minutes. Thereafter the reaction was stopped by addition of 25 µl 50% Glacial Acetic Acid. The Absorbance of released p-nitroaniline was read at 405 nm.

5. Inhibition of elastase activity was found only in fraction 19 of the tested portion, volume of this fraction was ca. 1900 µl. For control of the purity and the quantity of protein analytical sequence analysis were performed, resulting in indications that a mixture of peptides is present at a level of 1887 pMol, under assumption of an initial yield of 50%.

Figure 7:
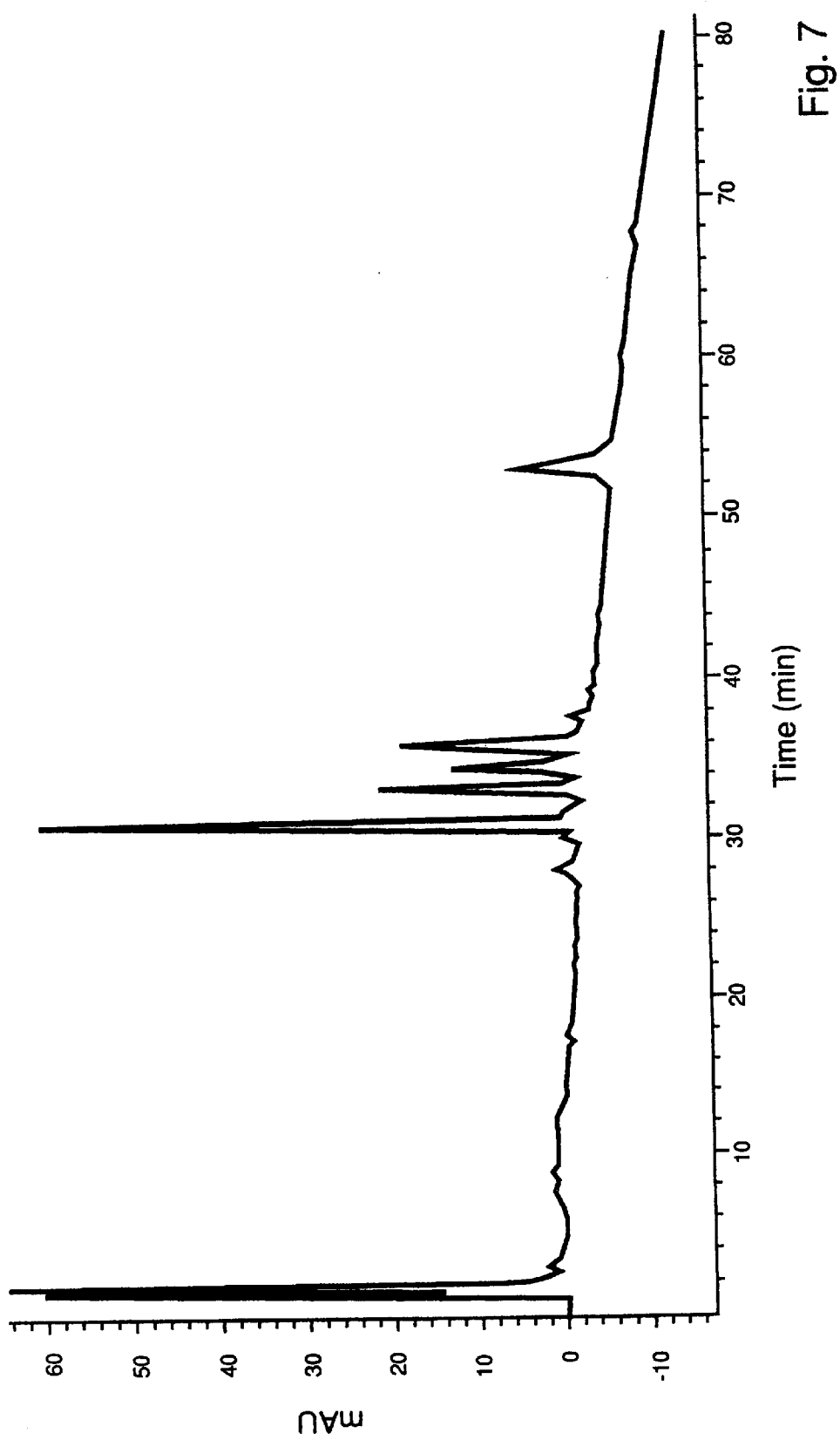

A chromatogram analytical HPLC of fraction 19 is presented in FIG. 7. Thereafter samples of peaks 5, 7, 8 and 9 were tested on elastase inhibition activity as described in the elastase inhibition assay procedure; only fractions 7, 8 and 9 showed inhibition of elastase. Fraction 5 did not show anti-elastase activity but a strong trypsin inhibition (see below).

6. Mass Spectrometry was performed with Laser Desorption. Within an accuracy of 01% the following masses were found for these fractions:

Fraction 5: 5377.2 and 5435.5 D (1:1 mixture)

Fraction 7: 5494.4 D.

Fraction 8: 5476.5 D.

Fraction 9: 5385.5 and 5454.1 D (1:1 mixture).

We have named these substances as follows:

Fraction 5: FAHSIN T ½

Fraction 7: FAHSIN E 1

Fraction 8: FAHSIN E 2

Fraction 9: FAHSIN E ¾.

7. Characterization with protein sequence analysis. Peak 7, 8 and 9 were analysed with standard Edman degradation. Various digestive steps (trypsin digest, NaOH incubation for Asn-Gly split, Glu-enzyme digest) led to the complete sequence of fraction 8, and the partial sequences of fractions 7 and 9. The molecules are apparently not glycosylated. Complete amino acid sequence of fraction 8 leads to the molecular mass of 5476, which corresponds well with the result of the MS: 5476.5.

The incomplete amino acid analysis of fraction 7 leads to, (supposing:

a) cysteines occur at the same positions as in fraction 8, b) all cysteines are involved in S—S bridging, c) Tyr-30 is the only substitution within residues 28 to 41 as compared to the sequence in fraction 8, d) No further substitutions occur after residue 41 as compared to the sequence in fraction 8,) the calculation of a molecular mass of 5493, which corresponds well with the result of the MS: 5494.4

The primary sequence (SEQ ID NO:2) is the following amino acid sequence of peak 8, which was found to be a single molecule. (N-terminal): Asp-Asp-Asn-Cys-Gly-Gly-Lys-Val-Cys-Ser-Lys-Gly- Gln-Leu-Cys-His-Asp-Gly-His-Cys-Glu-Cys-Thr-Pro-Ile-Arg-Cys- Leu-Ile-Phe-Cys-Pro-Asn-Gly-Phe-Ala-Val-Asp-Glu-Asn-Gly-Cys- Glu-Leu-Pro-Cys-Ser-Cys-Lys-His-Gln :( Carboxy-terminal)

Isoforms SEQ ID NO:7:

1. One other single molecule isoform was found in peak 7 (FIG. 7), its sequence from the N-terminus is: Asp-Asp-Asp(Cys)Gly-Gly-Gln-Val(Cys)Ser-Lys-Gly-Gln-Leu(Cys) His-Asp-Gly-His(Cys)Glu(Cys)Thr-Pro-Ile-Arg(Cys,Leu, Ile,Tyr, Cys,Pro,Asn,???,Phe,???,Val,Asp,Glu,???,???)

2. Another isoform, which was found to be a mixture of two molecules was found in peak 9 (FIG. 7), starts from the N-terminus as follows (SEQ ID NO:8 or SEQ ID NO:9): Asp-Asp-Asp(Cys)Gly-Gly-Lys-Val(Cys)Ser-Lys-Gly-Gln-Leu-(Cys) Gly Asn Gln Val-Asp-Gly-His(Cys)Glu(Cys)Thr-Pro-Ile-Arg(Cys)Leu-Ile-Tyr-Gln Lys (Cys,Pro)Asn-Gly (Phe,Ala,Val,???,Glu,Asn,Gly,Cys,???,???,???)

Further research on the nature and the activities found in the fractions corresponding to the peaks of FIG. 7 revealed that the fractions corresponding to the three peaks 7, 8 and 9, had a specific (elastase) activity of 1.2 IU/mg, 1.7 IU/mg and 0.95 IU/mg, respectively.

International units (IU) are defined as that quantity which reduces the enzymatic hydrolysis of SAAAP with 1 µmol/min at pH 8.3 and 25° C.

The fraction corresponding to peak 5 of FIG. 7 which for obvious reasons seems of interest (it is the largest peak) was also tested for its elastase activity. Said specific activity turned out to be less than 0,06 IU/mg, which means that the fraction corresponding to peak 5 contains no (hardly any) elastase-activity.

However, when further analyzing the fraction corresponding to peak 5, it revealed a strong activity in inhibiting trypsin. This trypsin inhibitory activity is at least twenty times higher than that of the fractions corresponding to peaks 7, 8 and/or 9.

Trypsin inhibition is a very useful activity, therefor we analyzed the amino-acid sequences present in the fraction of peak 5. We found a 1:1 mixture of 2 peptides, which were analyzed by LD-MS in the same manner as the fractions corresponding to peaks 7, 8 and 9. The analysis revealed molecular weights for the two peptides of 5377.2 and 5435.5 Dalton.

Sequencing of the peptides revealed the following sequences (SEQ ID NO:5 or SEQ ID NO:6):

```
                1            5              10                 15
     Asp-Asp-Asp-Cys-Gly-Gly-Gln-Val-Cys-Ser-Lys-Gly-Gln-Leu-Cys-
             Gly Asn 16           20             25                 30
     Val-Asp-Gly-Gln-Cys-Lys-Cys-Thr-Pro-Ile-Arg-Cys-Arg-Ile-Tyr-
```

```
                          -continued
   31             35                40                  45  ,
Cys-Pro-Lys-Gly-Phe-Glu-Val-Asp?-Glu-Asn-Gly-Cys-Glu-Leu-Pro- 46             50
Cys-Thr-Cys-Lys?-Gln?
```

The double residues indicated at positions two and three indicate the existence of the earlier mentioned mixture of two peptides.

These substances are named FAHSIN T ½.

Amino acid analysis of fraction 5 (FIG. 7) leads to, (supposing:
- a) cysteines occur at the same positions as in fraction 8,
- b) all cysteines are involved in S—S bridging,) the calculation of a molecular mass of 5437 and 5387, which corresponds well with the result of the MS. Amino Acid analysis of fraction 5 (FIG. 7) shows an unusual and unknown peak at between 10 and 12 minutes. It is speculated, that this may or may not be protein material, and may have certain biological effects not related to inhibition of Trypsin nor Plasmin.

An assay was developed for determination of the activity of this Trypsin inhibitor. In analogy with the elastase inhibition assay the preparation of the solution was as follows:

Trypsin, Type II-S soybean trypsin inhibitor (Sigma T 9128) and BAPNA (Sigma B 3279). This was further optimized to: trypsin solution: 120 µg/ml; BAPNA solution 10 mM; Trypsin inhibitor 100 µg/ml and incubation at 37° C. All other details were equal with the elastase inhibition assay.

The (significant) replacements of residues in these two peptides when compared with the peptides of the fraction of peak 8 (and 7 and 9 as far as possible) are printed bold. These changes are position 28 Leu to Arg, position 33 Asn to Lys, position 36 Ala to Glu and possibly position 47 Ser to Thr. When compared with the amino acid sequence of the fraction of peak 8, the length of these fraction 5 trypsin inhibitors may be reduced by one carboxy-terminal residue to a total of fifty residues.

Methods for de novo synthesis

In order to obtain sufficient quantities of the compositions of matter according to the invention, one can use known gene technological methods (see: Sambrook, T, et al: Molecular cloning: A laboratory Manual, Cold Spring Harbor Press, N.Y., USA., 1989). Four well-known methods, forming part of the known state of art, can be used for such synthesizing of the composition of matter.

First: Chemical addition technique in which the various amino acids are added: peptide synthesis (see Merrifield).

Second: After the synthesizing of an oligonucleotide, which bases correspond to the amino acid sequence as defined in this invention, such oligonucleotide is consequently built into a plasmid vector system, which then is brought into a useful bacterial or fungal carrier, which is then grown. Finally the synthesized molecule is retrieved from the cultures.

Third: The method for production and hybridisation of cDNA-libraries is in the art (see: Sambrook, T, et al, Molecular cloning: A laboratory Manual, Cold Spring Harbor Press, N.Y. USA., chapters 7, 8 and 11, 16 and 17). After elaboration of such a DNA library, identification of the genome which is coding for the protein sequence is searched. Thereafter, according to wellknown methods, the genome can be expressed in eukaryotic cells, yeasts, bacteries, and the protein can be acquired in larger quantities.

Fourth: The cells producing the protein can be cultivated in a monoculture and the protein is derived therefrom.

HIV-inhibition.

Fahsin was found to be active against HIV-1 and HIV-2 isolates in peripheral blood mononuclear cells (PBMC) and in primary macrophages.

Experimental:

Phytohaemagglutinin (PHA) stimulated PBMC from healthy donors were inoculated with two different HIV isolates (HIVAms 37 and HIVAms 55). After a two-hour exposure to the HIV isolates, the inoculum was removed and serial concentrations Fahsin were added to the cultures. Medium was changed twice a week, fresh PMA-stimulated PBMC were added avery week. Buffy-coats are routinely screened for viral contaminants and used only when negative for these contaminants. Virus production in the ceultures was monitored with a p24-capture ELISA, detecting p24 core protein of HIV. Cultures were also monitored for the occurence of cytopathic effects (syncytium formation).

High titre inocula of two primary syncytium inducing HIV isolates were prepared. Titers of stock were determined in a TCID50 assay.

During the first two days after isolation of the cells, primary peripheral blood leukocytes were cultured in Iscove's Modified Dulbecco's Medium (IMDM), supplemented with 10% foetal calf serum (FCS), polybrene (5(g/ml), phytohaemagglutinin (5(g/ml), penicillin (100 IU/ml) and streptomycin (100 IU/ml). The T-cell blasts were then further cultured in IMDM supplemented with 10% FCS, polybrene (5(g/ml), recombinant IL-2 (10 U/ml), penicillin (100 IU/ml) and streptomycin (100 IU/ml).

A total of 107 PHA-stimulated PBMC were inoculated with 104 TCID50/ml of the primary HIV isolates in a volume of 1 ml for 2 hours at 37° C. After 2 hours, cells were washed in a total volume of 30 ml. After centrifugation, supernatant was discarded to remove non-absorbed virus. Cells were subsequently resuspended to a final concentration of 106/ml.

From each cell suspension 100 µl aliquots containing 105 cells were transferred to wells of a 966 well tissue culture plate. Dilutions of Fahsin were made in culture medium in such a way that after addition of 50 µl to each well the final concentrations in the wells was 0.125 µM, 0.25 aM, 0.5 µM and 1.0 µM. Cells that received only medium served as untreated control cultures. Each concentration was analyzed in four fold. Cells were cultured in a humidified atmosphere at 37° C., 5% CO. Addition of 105 fresh PHA stimulated PBMC and medium was performed on day 7. In parallel, a new dose of the same concentrations of Fahsin was added.

Controls: On days 4 and 7, cultures were analyzed for any HIV-induced cytopathis effect as reflected by the presence of syncytia. At days 7, and 14, 30 µl of the culture supernatant was harvested to analyze the presence of p24 antigen in a p-24-antigen-capture-ELISA. For this, twice a week, 30 µl aliquots were harvested from the cultures and inactivated by the addition of 30 µl 0.2% Triton-X-100. 15 µl of this mixture was added to wells of a 96 well ELISA plate coated for 2 hours at 37° C. with an anti-p24 antibody shown to recognize all HIV isolates. Antigen was allowed to bind during 2 hours at 37° C. Bound p24 was detected with horseradish peroxidase-labelled rabbit-anti-p24 immunoglobulin (90' at 37° C.). Then, substrate (TMB) was added and after 20', the reaction was stopped by the addition of H2SO4.

Results are presented in FIGS. 8a through 8d.

The two Fahsin substances corresponding to the tested substances are:

Substance 1: Combination of Fahsin E 1-4 and Fahsin T 1-2.

Substance 2: Total leech body extract as presented under the deading "description of isolation".

Results showed that both substances have inhibitory effects on the replication of two primary isolates HIVAms 37 and HIVAms 55.

The results are arrived at in the following manner:

CALCULATION OF RESULTS

For the calculation of the percentage inhibition the following formula was used:

$$\text{Percentage inhibition} = \frac{\text{p24 production in untreated cultures} - \text{p24 production in cultures exposed to substance}}{\text{p24 production in untreated cultures}} \times 100\%$$

CRITERIA

Cultures were considered positive if:

Syncytia formation was observed on at least one occasion (cultures were examined twice a week) in combination with an elevated p24 antigen content in the supernatant on at least one occasion.

Syncytium score:

−no syncytia observed in any of the four replicate cultures

±syncytia observed in one out of four replicate cultures

+syncytia observed in two out of four replicate cultures

++syncytia observed in three out of four replicate cultures

+++syncytia observed in four out of four replicate cultures

RESULTS

HIV-1 induced cytopathic effects (CPE), production of p24 antigen, and calculated percentages inhibition are demonstrated in Tables in FIGS. 8a and 8b for substance 1, in Tables in FIGS. 8c and 8d for substance 2.

Data for p24 production represent the mean of four replicate cultures.

Cultures inoculated with $10^2$ TCID$_{50}$ remained negative for virus production.

Comparison with known molecules.

Comparison of the molecule (1) with known molecules from databanks gave the following results:

No homology, nor identical peptide stucture was found between the sequences of Fahsin, Eglin (Seemueller), and Gelin (PCT/NL90/46).

1. With Antistasin- Hydra magnipapillata (S29195): 15 derivates identity (29.4%) in 29 aa overlap.
2. With Transforming growth factor beta-1 binding protein (A35626): 15 derivates identity (29.4%) in 31 aa overlap.
3. With Fibrillin, human (L13923 and X63556): 17 derivates identity (33.3%) in 52 aa overlap.
4. With LDL receptor-related protein precursor, human (S02392): 10 derivates identity (19.6%) in 29 aa overlap.
5. Alpha-2-macroglobulin receptor, mouse ( S25111): 10 derivates identity (19.6%) in 29 aa overlap.
6. With VLDL receptor, human (D16493 and D 16494): 7 derivates identity (13.7%) in 11 aa overlap.
7. With Alpha-2-macroglobulin receptor, human (S30027): 10 derivates identity (19.6%) in 29 aa overlap.
8. With thrombospondin precursor, human (A26155): 12 derivates identity (23.5%) in 48 aa overlap.
9. With Anticoagulant Protein Ghilanten, H. Ghilianii (A34816) 16 derivates identity (31.4%) in 46 aa overlap.
10.
11. With Complement Pro-C3 precursor, human (A37156) 10 derivates identity (19.6%) in 25 aa overlap.
12. With Hepatitis C-virus mRNA (M96362) 8 derivates identity (15.7%) in 17 aa overlap.
13. With Antistasin, from Haementeria officinalis (A34398 & S13904): 17 derivates identity (33.3%) in 47 aa overlap.

Stability of the molecule Fahsin E2.

Stability of the molecule was tested a) by boiling it in water at 100° C. for 30 minutes.

b) by immersion in 50% acetic acid at room temperature during one night, and c) by immersion in 0.1M HCl in the same conditions.

The samples were consequently assayed with the elastase inhibition assay, as were blancs without inhibitor.

Results have shown no significant decrease of inhibiting activity in the samples. Therefore, it was concluded, that this molecule is extremely resistant to degradation by high temperatures and strong acid.

Possible active sites.

A database search was performed to estimate the probability for the active site. Prediction of structure resulted in:

No Helical conformation, 15.6% in extended conformation, and 84.3% in coil conformation A predicted beta-turn was likely to be the active site as is usual with most serpins (exposed binding loop). Aa 28–32 have a high probability for such an extended conformation, with residue 28 being the most exposed. It is known, that elastase inhibitors often have a Pro at P4', whereas trypsin inhibitors have an Arg at P1. We have concluded provisionally that the active site resides in Leu/Arg 28.

Manufacturing of a synthetic peptide inclusive of the proposed active site gave the following evidence.

Synthetic linear peptide: N-Acetyl-TPIRAbuLIFAbuPNGFAVD-amide(I)(SEQ ID NO:10), mimicking the residues 23 to 38 included, as elastase inhibitor and Synthetic linear peptide: N-Acetyl-TPIRAbuRIYAbuPKGFEVD-amide(II)(SEQ ID NO:11) mimicking the residues 23 to 38 included, as trypsin inhibitor, were produced from the C-terminus to the N-terminus on a 10(mol scale using solid-phase FMOC chemistry. Abu is 2-aminobutyric acid a cysteine ana. The crude peptides are partly purified by several ether-precipitations. A 15-mer, 10 mg of partly purified product is obtained. From this 10 mg a part of 7 mg consists of peptide material, of which at least 50% of the desired full length product, and a part of 3 mg of salts and remaining solvent (mainly water).

The quality of the final product was checked by sequence analysis, aminoacid analysis, LD-MS and RP-HPLC.

Synthetic peptide I (elastase inhibitor) shows a dose-dependent inhibition of elastase activity. Specific effectivity is about a factor 5,000 less than the native molecule, which is indicating both the active site and high efficiency of the synthetic peptide.

Synthetic peptide II (trypsin inhibitor) shows a dose-dependent inhibition of trypsin activity. Specific effectivity is about a factor 1,500 less than the native molecule, which is indicating both the active site and an even higher effeciency of the synthetic peptide.

Range of activities.

Fahsin E 1-4 was found to be strongly active as an inhibitor of human neutrophil elastase, pancreas elastase, chymotrypsin, but not of pepsin. Fahsin T 1-2 was found to be strongly active as an inhibitor of trypsin and plasmin. Fahsin was found to have strong antibiotic activity against Aeromonas species. Elastase inhibitory activity of Fahsin was measured by inhibition of the release of the p-nitroanilide group from the synthetic substrate N-succinyl-(Ala) 3-p-nitroanilide (SAAAP) (Calbiochem), catalyzed by pancreatic elastase and human neutrophil elastase respectively. Chymotrypsin inhibition activity of Fahsin was measured by the use of the synthetic substrate S-2586 (Kabi Vitrum). Trypsin activity of Fahsin was measured by the use of the synthetic substrate S-2238 (Kabi Vitrum). pepsin activity of Fahsin was measured by the use of a haemoglobin substrate. Trypsin inhibition activity was determined using the BAPNA assay. Plasmin inhibition activity of Fahsin was related with the Trypsin inhibition activity and measured by the use of the chromogenic substrate D-Val-Leusyl-Lys-pNA (Othodiagnostics).

Fahsin was also found to be active against HIV-1 and -2 replication in peripheral blood mononuclear cells (PBMC) and in primary macrophages. The inhibition was experimentally achieved by inoculation of PBMC from healthy donors with HIV isolates HIVAms 37 and HIVAms 55.

Inhibition was detected by the occurence of HIV-induced cytopathic effects (syncytium formation) in cultures with dilution series of the various Fahsin substances, as well as the p24 antigen capture ELISA.

Fahsin was also found to be able to dissolve fibrin. This was measured by the use of Cow's thrombin (Sigma T 6634) which was incubated with Cow's fibrinogen (Miles 82-0222-4), leaving stable fibrin clots. After incubation of this clot with the protein, which subsequently led to the measurement of free protein substance. This is in agreement with our macroscopic observations of clot-lysing potential of the live leech.

Fahsin was also found to be an effective thrombin inhibitor. This activity was determined by measuring the inhibition of the clotting activity of thrombin upon fibrinogen as was earlier described (Markwardt, 1970).

All substances Fahsin from *L. nilotica* have low potential for antigenic effect, as was oberved from the remarkable way of living of this leech. Therefore, therapeutic use of (natural) molecules from *L. nilotica* as described herewith, and (natural) molecules from *L. nilotica* still being determined-, as well as natural and synthetic mimicks of these natural molecules, will have a low immunogenicity.

Literature:

Autrum H.: Hirudineen. Systematik. In Bronn's Klassen und Ordnungen des Tierreichs, Bd. 4 abt. III, Buch 4, T. 1 1936: 1–96.

Blaise M,: Accidents occasionnes par les sang-sues. J Med Vet militaire 1874–1875; 10.

Blankenship D. T., Brankamp R. G., Manley G. D., Cardin A. D.: Amino sequence of ghilanten: anticoagulantantimetastatic principle of the South-American leech Haementeria ghilianii. Biophys Res Comm 1990; 166: 1384.

Budzynski A. z., Olexa S. A., Brizuela B. S., Sawyer R. T., Stent G. S.: Anticoagulant and fibrinolytic properties of salivary proteins from the leech Haementeria ghilianii. Proc Soc Exp Biol Med 1981; 168: 266.

Condra C., Nutt E., Petrowski C. J., Simpson E., Friedman P. A., Jacobs J. W.: Isolation and structural characterisation of a potent inhibitor of coagulation factor Xa from the leech Haementeria ghilianii. Thromb Haemost 1989; 61: 437.

Edman P. Acta Chem Scand 1956; 10: 761–768.

Fritz H., Krejci K.:Trypsin-plasmin inhibitors (Bdellins) from leeches. Meth Enzymol 1976; 45: 797.

Gasic G. J., Viner E. D., Budzynski A. Z., Gasic G. P.: Inhibition of lung tumour colonisation by leech salivary gland extracts from haementeria ghilianii. Cancer research 1983; 43: 1633.

Ghedia S.:Contribution±l'Étude des Hirudinees.Thesis, Sidi Thabet, Tunisie, 1984.

Hewick R. M., Hunkapiller M. W., Hood L. E., Dreyer W. J.: J Biol Chem 1981, 15: 7990–7997.

Harant H.:Essai sur les HirunidÉes. Arch Soc Sci Montpellier 1927, 10 : 1–76.

Ilse D., Edman P.:Aust J Chem 1963, 16: 411–416.

Jarry D.: Sur la presence de Limnatis nilotica dans un oued meditarraneen: la baillaurie a Banyuls-sur-Mer.Bull Soc Zool Fr 1959, 84; 73–76.

Keegan H. L., Radke G., Murphy D. A.: Nasal leech infestation in man Am J Trop Med Hyg 1970, 19-6: 1029–1030.

Kirschbaum N. E., Budzynski A. Z.: A unique proteolytic fragment of human fibrinogen containing the Aa-COOH-terminal domain of the native molecule. J Biol Chem 1990; 265: 489.

Markwardt F: Die antagonistische Wirkung des Hirudins gegen Thrombin in vivo. Naturwissenschaften 1956; 43: 111.

Markwardt F: Hirudin as an inhibitor of Thrombin. Meth Enzymol 1970; XIX: 924.

Markwardt F: The come-back of hirudin: an old established anticoagulant agent. Folia Haematol 1988; 115: 10–23.

Mouquin-Tandon A.:Monographie de la famille des HirunidÉes. Paris, 1846.

Neveu-Lemaire.:Traitéd'entomologie médicinale et véterinaire.1938.

Petersen T. E., Roberts H. R., Sotrup-Jensen L., Magnusson S.: Primary structure of hirudin, a thrombinspecific inhibitor. In: Protides of the biological fluids. Ed: Peters. Pergamon Oxford 1975: 145–149.

Seemuller U.: Inhibitoren aus dem Blutegel Hirudo medicinalis mit Hemmwirkung gegen chymotrypsin, subtilisin, und die menschlichen Granulozytenproteasen elastase und kathepsin G. Ph D Dissertation, Munich University, 1979.

Turner F. M,: Pharyngial leeches.The Lancet 1969, dec '27, 1400–1401.

What is claimed is:

1. A substance having protease inhibiting activity comprising an isolated polypeptide that comprises residues 23 to 38 of an amino acid sequence selected from the group consisting of SEQ ID NOs.: 2, 3.

2. A substance according to claim 1 which inhibits elastase, chymotrypsin, trypsin, thrombin, or plasmin.

3. A substance according to claim 1, which enhances the dissolution of fibrin.

4. A substance according to claim 1, which inhibits the replication of human immunodeficiency virus in human cells.

5. A substance according to claim 1 having antibiotic activity.

6. A substance according to claim 1 for use as a therapeutic.

7. A composition comprising a substance according to claim 1 together with suitable excipients.

8. An isolated nucleic acid molecule encoding the polypeptide according to claim 1.

9. An isolated nucleic acid molecule according to claim 8, comprising the sequence of SEQ ID NO:1.

10. An expression vector comprising a nucleic acid molecule according to claim 9 together with suitable control elements for expression.

11. An expression system comprising an expression vector according to claim 10.

12. An expression system according to claim 11, wherein the expression system is a recombinant host cell.

13. The substance according to claim 1 having the sequence of SEQ ID NO:10 or SEQ ID NO:11.

14. The substance according to claim 1 having the sequence of SEQ ID NO:2, SEQ ID NO:3 or SEQ ID NO:4.

* * * * *